(12) United States Patent
Stigall

(10) Patent No.: US 9,603,547 B2
(45) Date of Patent: Mar. 28, 2017

(54) HIGH PRESSURE THERAPEUTIC AND IMAGING CATHETER

(71) Applicant: Volcano Corporation, San Diego, CA (US)

(72) Inventor: Jeremy Stigall, Carlsbad, CA (US)

(73) Assignee: Volcano Corporation, San Diego, CA (US)

( * ) Notice: Subject to any disclaimer, the term of this patent is extended or adjusted under 35 U.S.C. 154(b) by 541 days.

(21) Appl. No.: 14/096,982

(22) Filed: Dec. 4, 2013

(65) Prior Publication Data

US 2014/0163358 A1 Jun. 12, 2014

Related U.S. Application Data

(60) Provisional application No. 61/734,825, filed on Dec. 7, 2012.

(51) Int. Cl.

| A61B 5/06 | (2006.01) |
|---|---|
| A61B 5/00 | (2006.01) |
| A61B 5/02 | (2006.01) |
| A61B 8/08 | (2006.01) |
| A61B 8/12 | (2006.01) |
| A61B 8/00 | (2006.01) |

(Continued)

(52) U.S. Cl.
CPC ............ *A61B 5/061* (2013.01); *A61B 5/0066* (2013.01); *A61B 5/02007* (2013.01); *A61B 5/6853* (2013.01); *A61B 8/0891* (2013.01); *A61B 8/12* (2013.01); *A61B 5/0075* (2013.01); *A61B 5/0095* (2013.01); *A61B 5/026* (2013.01); *A61B 5/0215* (2013.01); *A61B 5/4836* (2013.01); *A61B 8/445* (2013.01); *A61F 2/958* (2013.01)

(58) Field of Classification Search
CPC ... A61B 5/0066; A61B 5/0075; A61B 5/0095; A61B 5/02007; A61B 5/0215; A61B 5/026; A61B 5/061; A61B 5/4836; A61B 5/6853; A61B 8/0891; A61B 8/12; A61B 8/445; A61F 2/958
See application file for complete search history.

(56) References Cited

U.S. PATENT DOCUMENTS

| 5,116,317 A | 5/1992 | Carson et al. | |
| 2003/0203991 A1* | 10/2003 | Schottman | C08K 3/22 523/334 |

(Continued)

OTHER PUBLICATIONS

International Search Report and Written Opinion received in corresponding Patent Cooperation Treaty Application No. PCT/US2013/073095 dated Mar. 6, 2014, 18 pages.

(Continued)

*Primary Examiner* — Ruth S Smith

(57) ABSTRACT

Disclosed herein is an integrated therapeutic and imaging catheter. The catheter comprises an inner member defining a guidewire lumen, a balloon assembly, a treatment device mounted about the balloon assembly, and an imaging device. The balloon assembly comprises an inner sleeve surrounding the inner member and a connection medium, wherein the connection medium is disposed between the balloon inner sleeve and the inner member, and an outer sleeve surrounding the inner sleeve. The imaging device is disposed distal to the balloon assembly and is coupled to the connection medium.

19 Claims, 12 Drawing Sheets

(51) Int. Cl.
    *A61B 5/0215*    (2006.01)
    *A61B 5/026*     (2006.01)
    *A61F 2/958*     (2013.01)

(56) References Cited

U.S. PATENT DOCUMENTS

| | | | |
|---|---|---|---|
| 2004/0097804 A1 | 5/2004 | Sobe | |
| 2004/0143312 A1 | 7/2004 | Samson et al. | |
| 2006/0247603 A1 | 11/2006 | Gottlieb et al. | |
| 2006/0271154 A1* | 11/2006 | Woodall | A61B 17/12136 623/1.11 |
| 2006/0282153 A1 | 12/2006 | Jang | |
| 2008/0009829 A1* | 1/2008 | Ta | A61F 2/856 604/509 |
| 2009/0043191 A1* | 2/2009 | Castella | A61B 5/0066 600/425 |
| 2011/0060214 A1 | 3/2011 | Makower | |
| 2011/0125132 A1* | 5/2011 | Krolik | A61B 17/22032 604/509 |
| 2012/0253186 A1* | 10/2012 | Simpson | A61B 17/320758 600/426 |

OTHER PUBLICATIONS

International Searching Authority/European Patent Office, "Communication—Extended European Search Report," for European Application No. 13861192.6, mailed Jul. 7, 2016, 7 pages.

\* cited by examiner 44755.1283

REPLACEMENT SHEET

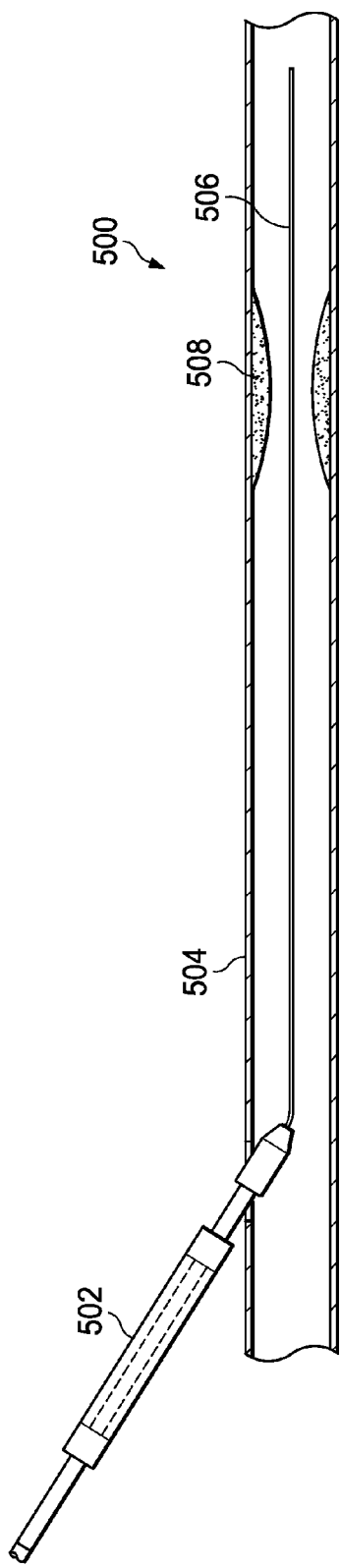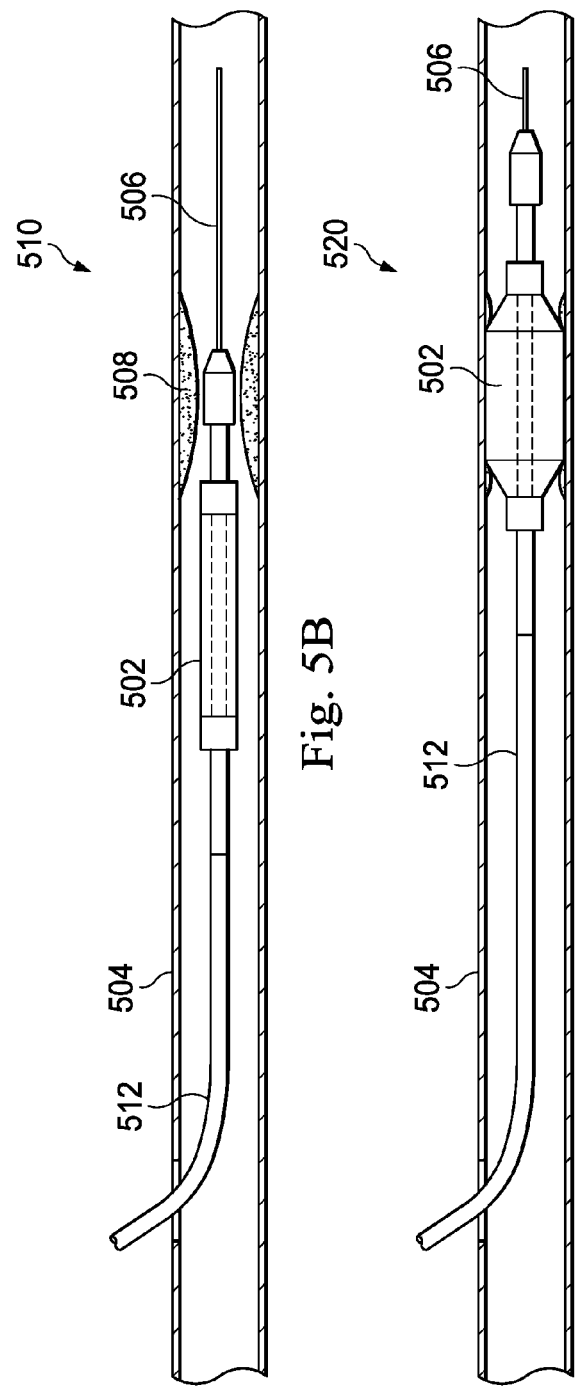

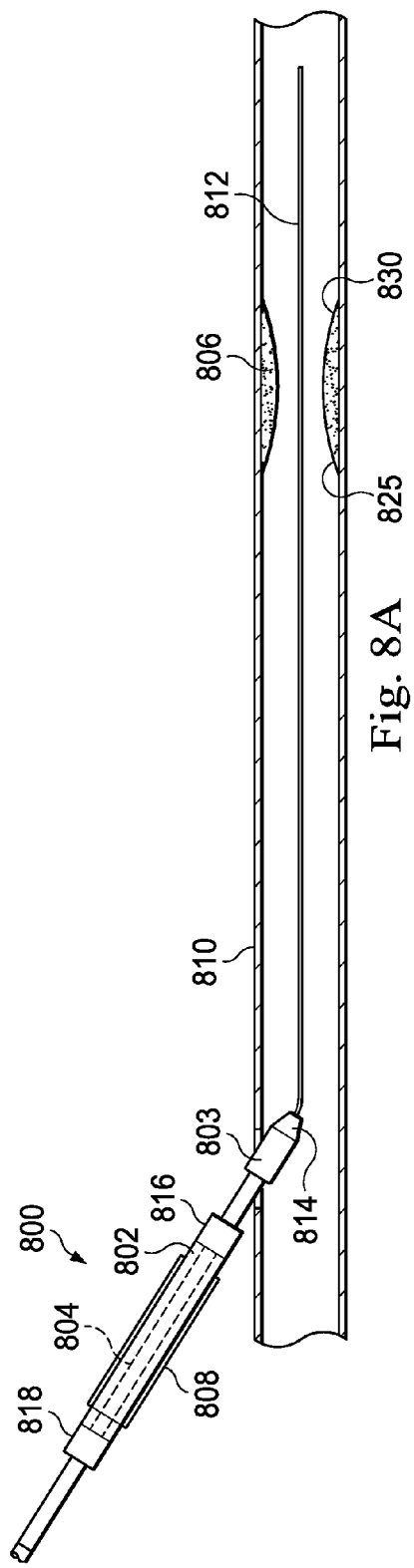
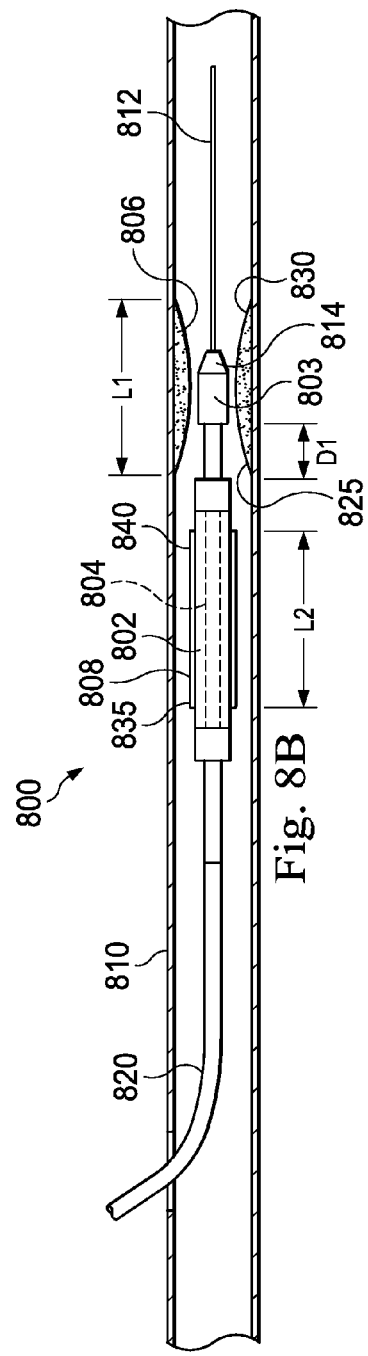
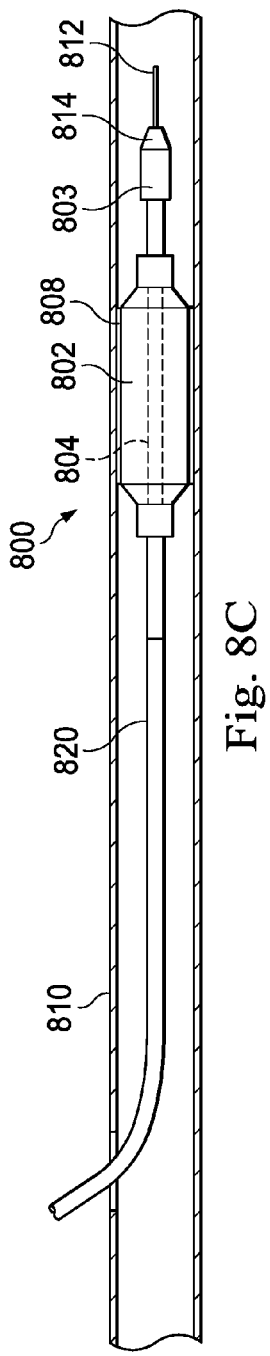
Fig. 8A
Fig. 8B
Fig. 8C

HIGH PRESSURE THERAPEUTIC AND IMAGING CATHETER

CROSS-REFERENCE TO RELATED APPLICATIONS

The present application claims priority to and the benefit of U.S. Provisional Patent Application No. 61/734,825, filed Dec. 7, 2012, which is hereby incorporated by reference in its entirety.

TECHNICAL FIELD

Embodiments of the present disclosure relate generally to the field of medical devices and, more particularly, to integrated therapeutic imaging catheters.

BACKGROUND

Intravascular imaging systems are widely used in interventional cardiology as a diagnostic tool for a diseased vessel, such as an artery, within the human body. Various sensors may be placed on a catheter and positioned in the body. One type of imaging system is an intravascular ultrasound (IVUS) system. In one example, a phased array IVUS device includes a number of transducers that are passed into a vessel and guided to an area to be imaged. The transducers emit ultrasonic waves in order to create an image of the vessel of interest. The ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Intravascular imaging systems are often used to detect arterial occlusions that can be relieved through use of a balloon catheter. A balloon catheter is a type of catheter with a balloon near the tip. The balloon catheter is designed to be inserted into a patient's artery and positioned to a spot where an occlusion was detected through use of an intravascular imaging system. Upon reaching the detected occlusion, the balloon is inflated to relieve the occlusion. In some instances, the balloon catheter includes a stent, and inflation of the balloon expands and deploys the stent within the vessel.

An intravascular imaging system may be integrated at the distal end of a balloon catheter. With such integration, the intravascular imaging system does not have to be first removed from the patient's artery before the balloon can be used to relieve the occlusion. Rather, upon detection of an occlusion, the catheter can be pushed further into the patient so that the balloon is aligned with the occlusion.

SUMMARY

The present disclosure provides devices, systems, and methods for imaging and treating an intravascular lesion without the need for exchanging between separate imaging and treatment devices. As a result, the surgical process and treatment of the patient are improved by reducing the amount of time needed for the procedure, which reduces the amount of time a patient may need to be under anesthesia, allowing for easy and convenient confirmation of proper application of the treatment via the integrated imaging, which leads to improved patient outcomes.

In one embodiment, the present disclosure describes an integrated therapeutic and imaging catheter. In one aspect, the catheter comprises an inner member, a balloon assembly, and an imaging device. In another aspect, the catheter comprises a balloon assembly, a treatment device, and an imaging device. In some embodiments, the inner member defines a guidewire lumen. In some embodiments, the balloon assembly comprises an inner sleeve surrounding the inner member and a connection medium, wherein the inner sleeve is configured to protect the connection medium when the balloon assembly is inflated. In one aspect, the connection medium is disposed between the balloon inner sleeve and the inner member. In some embodiments, the balloon assembly further comprises an outer sleeve surrounding the inner sleeve. In some embodiments, the treatment device is associated with the balloon assembly, and in some embodiments the treatment device is mounted about the balloon assembly. In some embodiments, the imaging device is disposed distal to the balloon assembly and coupled to the connection medium.

In another embodiment, the present disclosure describes a catheter. In one aspect, the catheter comprises a balloon assembly, a connection medium, and an imaging device. In another embodiment, the catheter comprises a balloon assembly, an imaging device, a treatment device, and a connection medium. In some embodiments, the balloon assembly comprises an inner balloon sleeve surrounding an inner member. In one aspect, the inner balloon sleeve defines a fluid-tight space therebetween. In some embodiments, the imaging device is disposed distal to the inner balloon sleeve and adjacent a distal end of the catheter. In some embodiments, the treatment device surrounds the balloon assembly. In some embodiments, the connection medium extends within the space between the inner member and the inner balloon sleeve. In one aspect, the connection medium connects the imaging device to a proximal end of the catheter. In some embodiments, the inner balloon sleeve is configured to collapse and protect the connection medium when the balloon assembly is inflated.

In another embodiment, the present disclosure describes a method for using a catheter in a vessel of a patient. In one aspect, the method comprises inserting a catheter including a balloon assembly, a connection medium, and an imaging device into the vessel. In some instances, the balloon assembly is separated from the imaging device by a first distance and the balloon assembly surrounds the connection medium. The method further comprises imaging a lumen of the vessel with the imaging device as the catheter is advanced through the vessel, and identifying and imaging a lesion within the lumen of the vessel with the imaging device. In some instances, the method further comprises measuring a length of the lesion as the imaging device is advanced through the lesion, and advancing the catheter by a second distance based on the length of the lesion and the first distance to position the balloon assembly relative to the lesion. In some instances, the method comprises positioning the balloon assembly within the lesion, and inflating the balloon assembly within the lesion using high pressure to compress the lesion against the lumen of the vessel without interfering with the connection medium.

BRIEF DESCRIPTION OF THE DRAWINGS

FIGS. 5A-5C are diagrams showing an illustrative insertion of a balloon catheter into a patient, according to one example of principles described herein.

FIGS. 8A-8F are diagrams showing an illustrative insertion of an integrated catheter into an artery of a patient, according to one example of principles described herein.

DETAILED DESCRIPTION

Figure 1A:
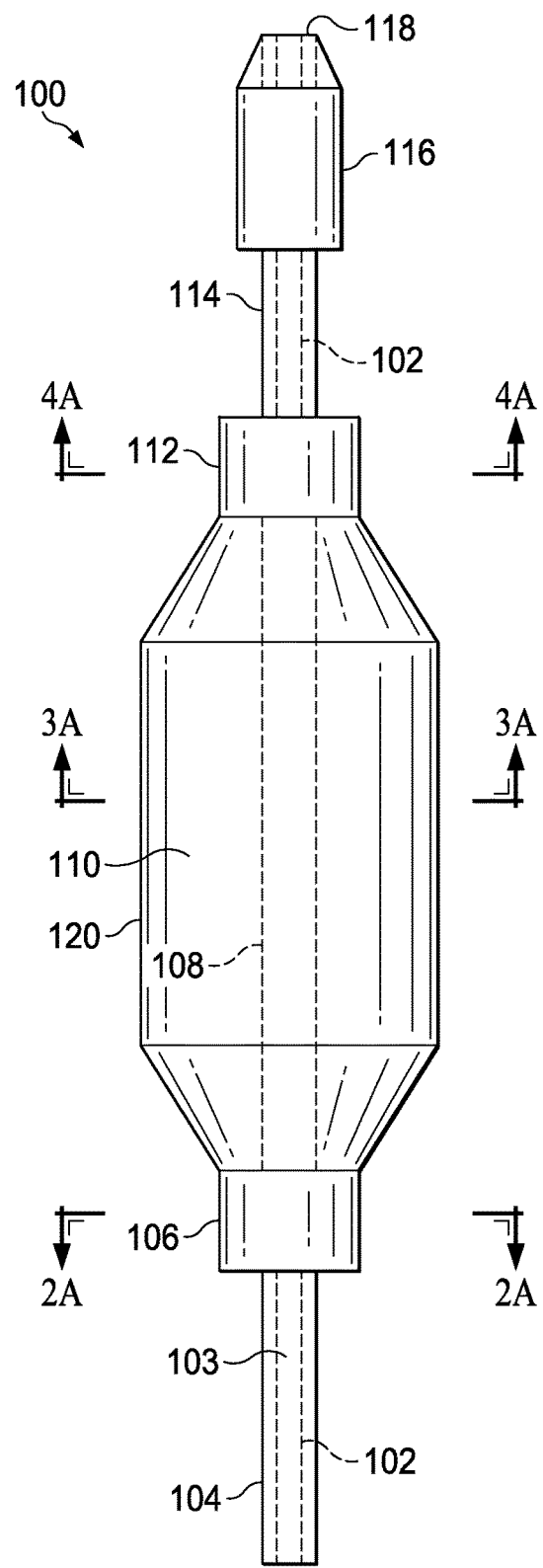
FIGS. 1A and 1B are diagrams showing illustrative sensing catheters, according to principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Embodiments disclosed by the present disclosure are directed to combination catheters that incorporate non-compliant therapeutic devices with imaging systems to accurately access, assess, and treat diseased vessels and/or other tubular structures within a patient. For example, embodiments of the present disclosure are configured to optimize stent placement and expansion. Some of the embodiments disclosed herein comprise balloon stent catheters that incorporate imaging devices such as, by way of non-limiting example, transducers and optical devices operable to perform sensing modalities such as IVUS, optical coherence tomography (OCT), photo acoustic inspection and spectroscopy. In some embodiments, the imaging elements may be oriented generally perpendicular to the axis of the device for side looking imaging while other embodiments may employ axially oriented imaging sensors that provide forward looking imaging ahead of the balloon assembly. Moreover, the embodiments disclosed herein provide a low profile and flexible device that allows for the utilization of high pressure systems with non-compliant therapeutic devices during imaging. Thus, the embodiments disclosed herein allow healthcare professionals to access, assess, and treat intratubular lesions, including arterial lesions, with more ease, less resistance, and more visibility than offered by some prior art catheters.

Figure 1B:
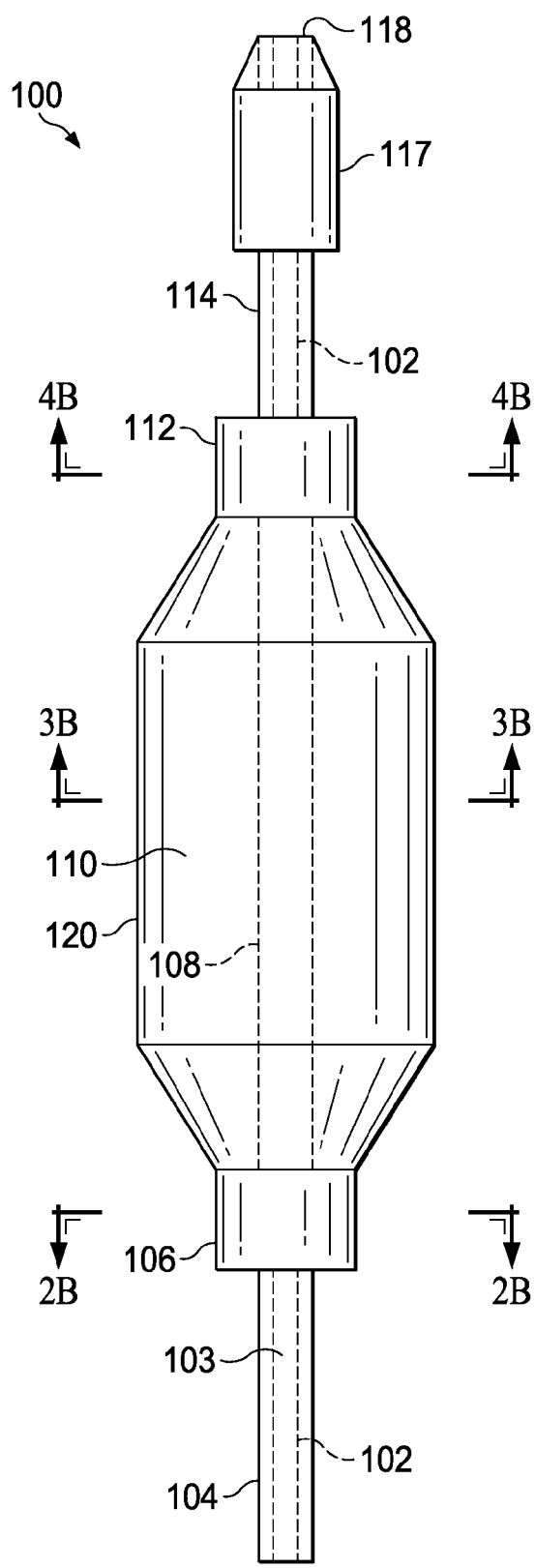

FIGS. 1A and 1B are diagrams showing illustrative balloon catheter 100 according to certain embodiment of the present disclosure. FIG. 1A illustrates a balloon sensing catheter having an electronically actuated sensor 116 while FIG. 1B illustrates a balloon sensing catheter having a sensor 117 that is rotated by a drive shaft. The components of the systems have many common elements which will be referred to by the same reference numbers throughout the disclosure. According to certain illustrative examples, the catheter 100 includes a balloon assembly 110 with an outer sleeve 120 and an inner sleeve 108. The balloon assembly 110 is joined to a proximal shaft 104 through a proximal junction 106. Additionally, the balloon assembly 110 is joined to a mid-shaft 114 through a distal junction 112. In the illustrated embodiment, the mid-shaft 114 extends between the balloon assembly 110 and a sensing device 116. An inner member 102 defining a guide wire lumen 103 runs from the tip 118 of the catheter, through the interior of the proximal shaft 104, the balloon assembly 110, and the mid-shaft 114, to at least the proximal end of the balloon assembly 110.

The proximal shaft 104 connects the balloon assembly 110 to a pressurized fluid system while a connection medium 208, such as electrical conductors or optical fibers, extending within the proximal shaft connect the sensing device 116 to a processing systems (not shown) at the proximal end of the catheter 100. In one aspect, the sensing device 116 is an ultrasound transducer array having a maximum outer diameter of 3.5 F and the connection medium 208 is a microcable having a braided exterior with 7 individual insulated electrical conductors. In another aspect, the connection medium comprises fiberoptics. In some embodiments, the connection medium 208 extends through the entire length of the balloon assembly 110 and joins the sensing device 116. The processing systems typically remain outside of the patient. The processing system uses the data received from the sensing device 116. When the sensing device 116 is part of an imaging system, the data can be used to create an image. The image can be displayed to a medical professional in real time as the catheter moves through the patient's artery. This allows the medical professional to find various occlusions or other irregularities which may exist throughout the patient's artery. In a similar manner, the sensing device 116 could be a pressure or flow sensor, and the processing system could determine fractional flow reserve values based on the sensed data.

The proximal shaft 104 is made of a plastic, polymer, metal, or other flexible material. In one aspect, the proximal shaft may include a metal proximal portion joined to a distal polymer tube with a metal wire embedded in the polymer tubing adjacent the coupling to transition the stiffness of the tubing from the stiffer metal to the more flexible polymer tubing. The proximal shaft 104 is designed to be flexible so that it may effectively traverse a patient's artery without damaging the artery. The proximal shaft 104 may be a dual lumen shaft. The dual lumen proximal shaft 104 may be an axial dual lumen shaft with an inner lumen and an outer lumen.

The proximal shaft 104 may have a diameter within the range of 2 to 4 French (i.e., 0.67 to 1.33 mm). The length of the proximal shaft 104 is long enough to allow the balloon 110 and the sensing device 116 to reach a sufficiently deep region of a patient's artery. For example, the proximal shaft 104 may have a length of approximately 150 cm. In a collapsed condition, the maximum outer diameter of the balloon assembly is approximately 0.040 inches.

The inner member 102 defines a guidewire lumen 103 that is sized to receive a guide-wire (shown in FIG. 5A). In one embodiment, the guidewire lumen has a diameter of 0.017 inches such that it can receive a 0.014 inch diameter guidewire. Typically, a guide-wire is first inserted into a patient's artery. The catheter is then placed over the guide-wire such that the inner member 102 encompasses the guide-wire. In some examples, the inner member 102 may extend the entire length of the catheter 100, from the tip 118 to the proximal end of the proximal shaft 104. Such a catheter is referred to as an over-the-wire catheter. In some examples, the inner member 102 may extend along a short distance and then exit out of the catheter at an exit port near the proximal end of the balloon 110. Such a catheter is referred to as a rapid exchange catheter.

The length of the inner member is long enough to extend from the point at which the catheter starts on the guide-wire (typically, the tip) to the point at which the guide-wire exits the catheter. Thus, the length may be relatively short in the case of a rapid exchange catheter and relatively long in the case of an over-the-wire catheter.

The mid-shaft 114 is connected between the distal end of the balloon 110 and the sensing device 116. The mid-shaft 114 is made of a polymer, plastic, or other flexible material. The mid-shaft 114 is flexible so that it may effectively traverse a patient's artery without damaging the artery. The inner member 102 runs through the interior of the mid-shaft 114. Additionally, a connection medium runs from the sensing device 116 towards the balloon 110 through the mid-shaft 114.

Figure 2A:
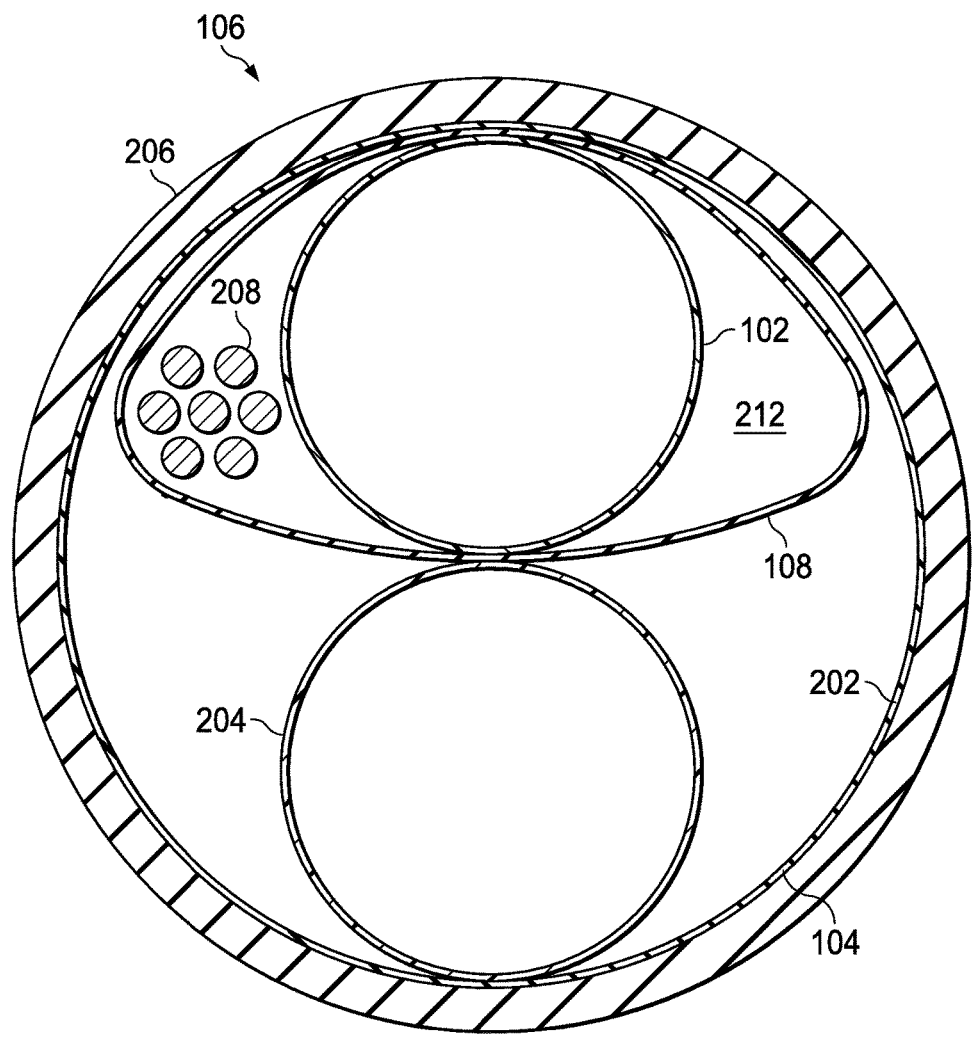
FIGS. 2A and 2B are diagrams showing an illustrative cross-section taken along line 2-2 of FIGS. 1A and 2B, respectively, of a proximal junction of a balloon catheter, according to one example of principles described herein.

FIG. 2A is a diagram showing an illustrative cross-section of a proximal junction 106 of the balloon catheter 100 according to one embodiment of the present disclosure. The proximal junction 106 connects the proximal end of the balloon to the proximal shaft (e.g., 104, FIG. 1A). According to certain illustrative examples, the proximal shaft is a dual lumen shaft that includes an inner lumen 204 and an outer lumen 202. The proximal junction 106 also includes the inner member 102, the inner balloon sleeve 108, and a space through which connection media 208 run. The proximal junction 106 further includes a balloon proximal leg 206. In one aspect, the balloon proximal leg 206 is an extension of the material forming the balloon outer sleeve 120.

Figure 2B:
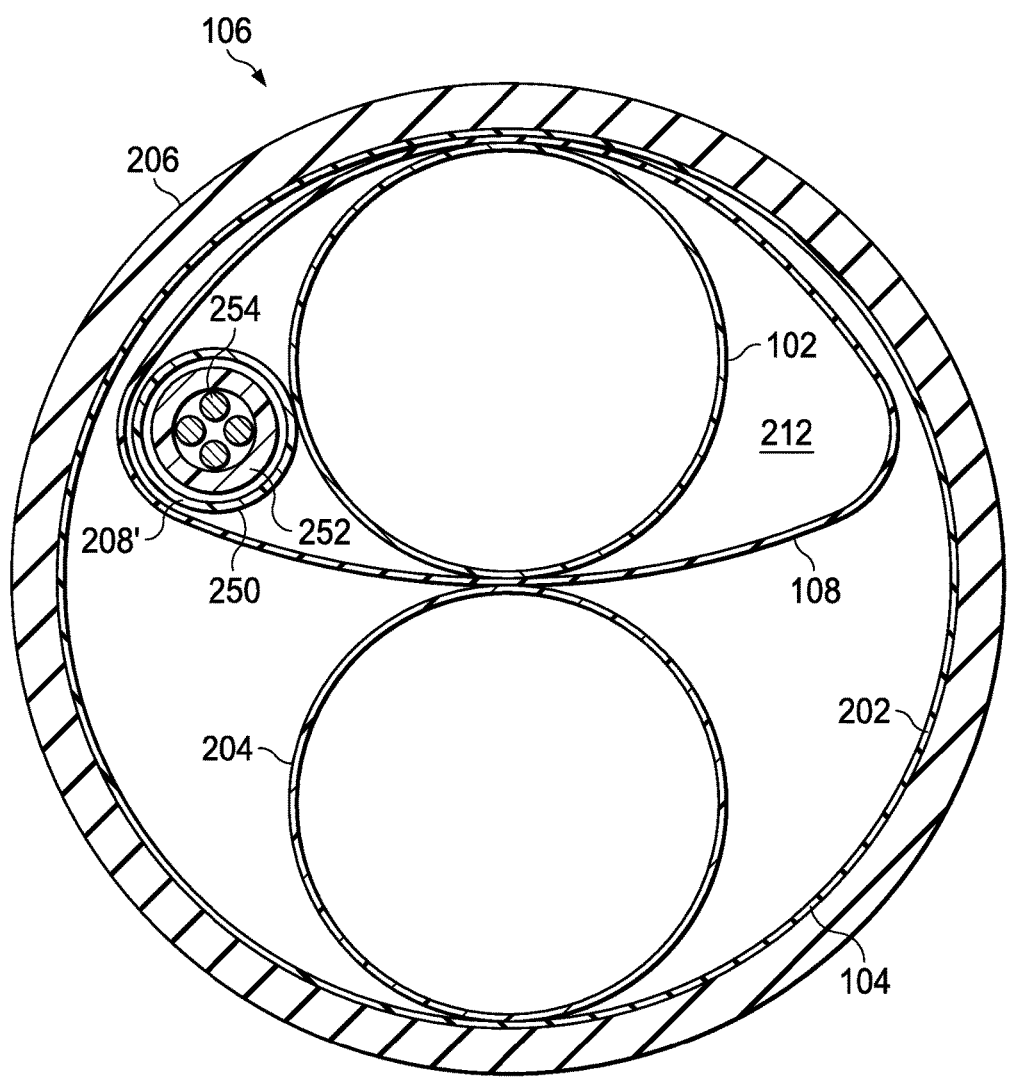

FIG. 2B illustrates a cross-sectional view of the embodiment shown in FIG. 1B. The embodiment of FIG. 2B includes an alternative connection media 208'; formed as a rotary drive cable assembly. The cable includes an outer sheath 250 surrounding an inner drive cable 252 and a series of electrical conductors or optical fibers 254.

The outer lumen 202 of the proximal shaft 104 provides an external structure for the proximal shaft 104. The inner lumen 204 is smaller in diameter than the outer lumen 202 and runs axially within the outer lumen 202. The size of the inner lumen 204 is such that there is sufficient room within the outer lumen for the inner member 102, inner balloon sleeve 108, and connection media 208.

The inner lumen 204 can be used to pump inflation fluid into the balloon. Thus, the end of the inner lumen 204 within the proximal junction 106 serves as an inflation port where the inflation fluid exits the inner lumen 204 into the balloon. The inflation fluid exits into the space between the balloon inner sleeve 108 and the balloon outer sleeve, thus inflating the balloon.

The balloon inner sleeve 108 acts as a barrier between the inflation fluid and any structures that run through the internal portion of the catheter, particularly, the connection media 208 and the inner member 102. The balloon inner sleeve 108 is bonded to the interior of the outer lumen 202 of the proximal shaft 104. Additionally the balloon inner sleeve 108 encompasses the inner member 102. As shown more fully in FIGS. 3A and 3B, the balloon inner sleeve 108 is sized such that there is a sufficient space 212 between the sleeve 108 and the inner member 102 so as to allow any connection media 208 or 208' to fit therein. This space 212 allows the connection media 208 or drive cable 208' to float freely without damaging the integrity of the balloon. However, bonding material 213 fills the space in the proximal connection 106 and distal connection 112 to define the fluid tight region 212 within inner sleeve 108 beneath balloon 120.

In one aspect, the inner sleeve 108 is formed of a multi-layer structure suitable for high pressure operation greater than 20 atmospheres (ATM). In some embodiments, the inner sleeve 108 is configured to be suitable for operating pressures extending through, by way of example only, a range of 15 to 25 ATM. In one aspect, this range may comprise 17 to 22 ATM. In another aspect, this range may comprise 19 to 21 ATM. Other ranges are contemplated. The material properties and construction of the inner sleeve 108 allow it to deform under high pressure without significant elongation along the longitudinal axis of the balloon assembly, even under the application of high pressures. In some embodiments, the materials forming the inner sleeve 108 permit very little, if any, axial compression and extension, even under the application of high pressures.

In one embodiment, the inner sleeve is formed by an inner layer of polyethylene (PE) bonded to an outer layer of maleated polyethylene. The outer layer of maleated PE is more suitable for heat treated bonding to other components of the system, such as the proximal shaft 104 and mid-shaft 114, that can be formed of PBAX. It will be understood that the proximal shaft 104, the mid-shaft 114, and the inner shaft 102 are formed such that they do not deform under high operating pressures while the inner sleeve 108 is designed to intentionally elastically deform inwardly under the high operating pressures of the balloon system. The inner sleeve 108 is shaped and configured to collapse around the connection media 208 or drive cable 208' without damaging or otherwise interfering with the operation of the connection media or drive cable running through the inner sleeve. The inner sleeve 108 then elastically returns to its original shape when the high pressure condition is removed. Return of the inner sleeve to its original shape may also be aided by the compressed gas within the space 212.

Various types of connection media may run through the space 212 between the inner member 102 and the balloon inner sleeve 108. For example, in the case that the sensing device produces electrical signals to be processed by external systems, then the connection media may include conductive wires to carry those electrical signals. Alternatively, the connection media may include fiber optic cables to propagate those signals in the form of light. The number of wires or cables depends on the type of sensing device and the manner in which data is transferred from the sensing device to the external processing systems. Conductive wires may also be used to provide electrical power to the sensing device.

In the case that the sensing device is rotational, the connection media 208 may include a driveshaft lumen. In one aspect, the driveshaft lumen may include a plastic sheath filled with a liquid lubricant. The lubricant allows the driveshaft running through the plastic sheath to spin with a minimal amount of friction against the interior of the plastic sheath.

The balloon proximal leg 206 is part of the balloon outer sleeve (e.g., 120, FIG. 1A). The balloon proximal leg 206 is designed to fit securely around the exterior of the proximal shaft 104. The balloon proximal leg 206 may be bonded to the exterior of the proximal shaft through a variety of bonding methods. These bonding methods include, but are not limited to, thermal bonding and laser bonding.

Figure 3A:
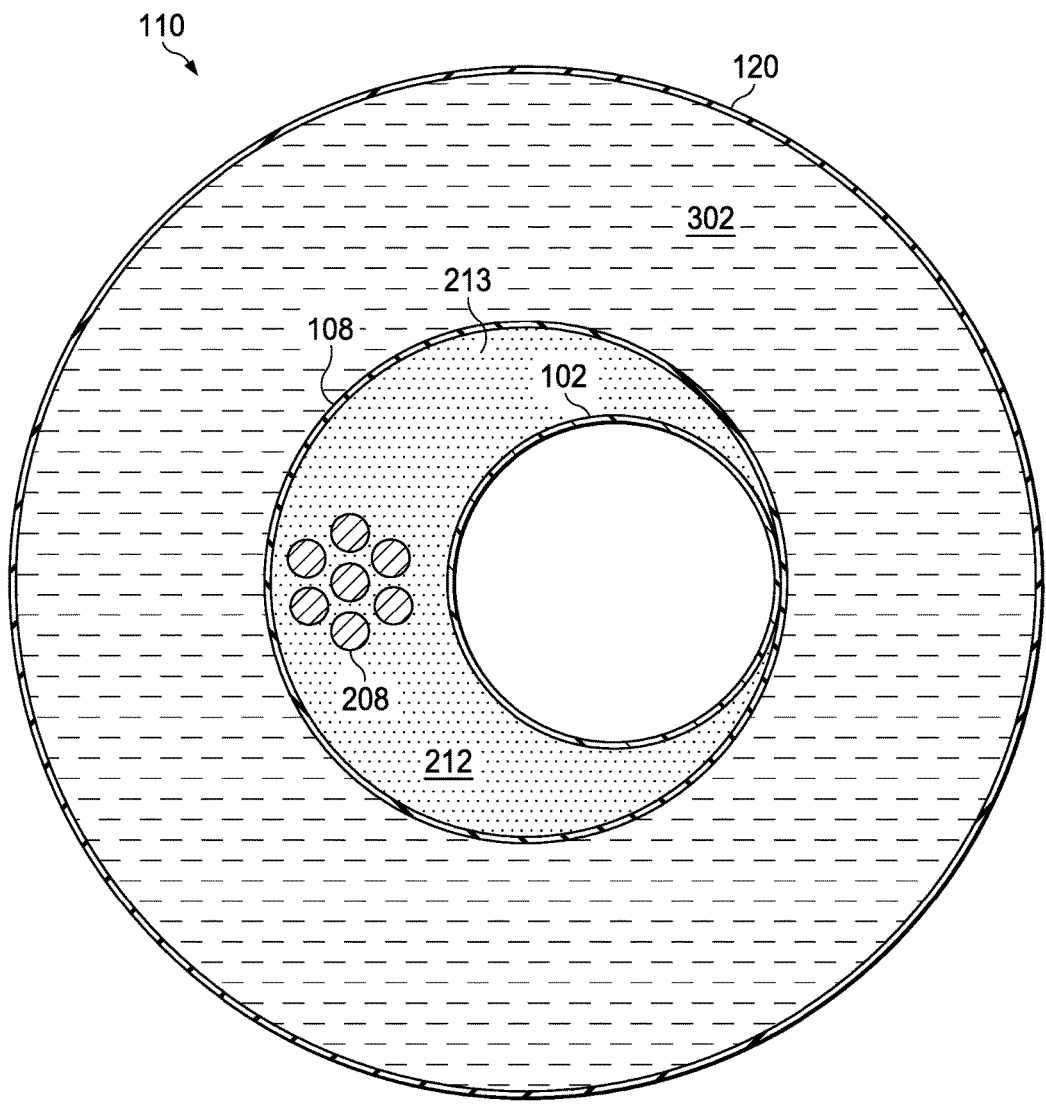
FIGS. 3A and 3B are diagrams showing an illustrative cross-section of a balloon taken along line 3-3 of FIGS. 1A and 1B, respectively, according to one example of principles described herein.
Figure 3B:
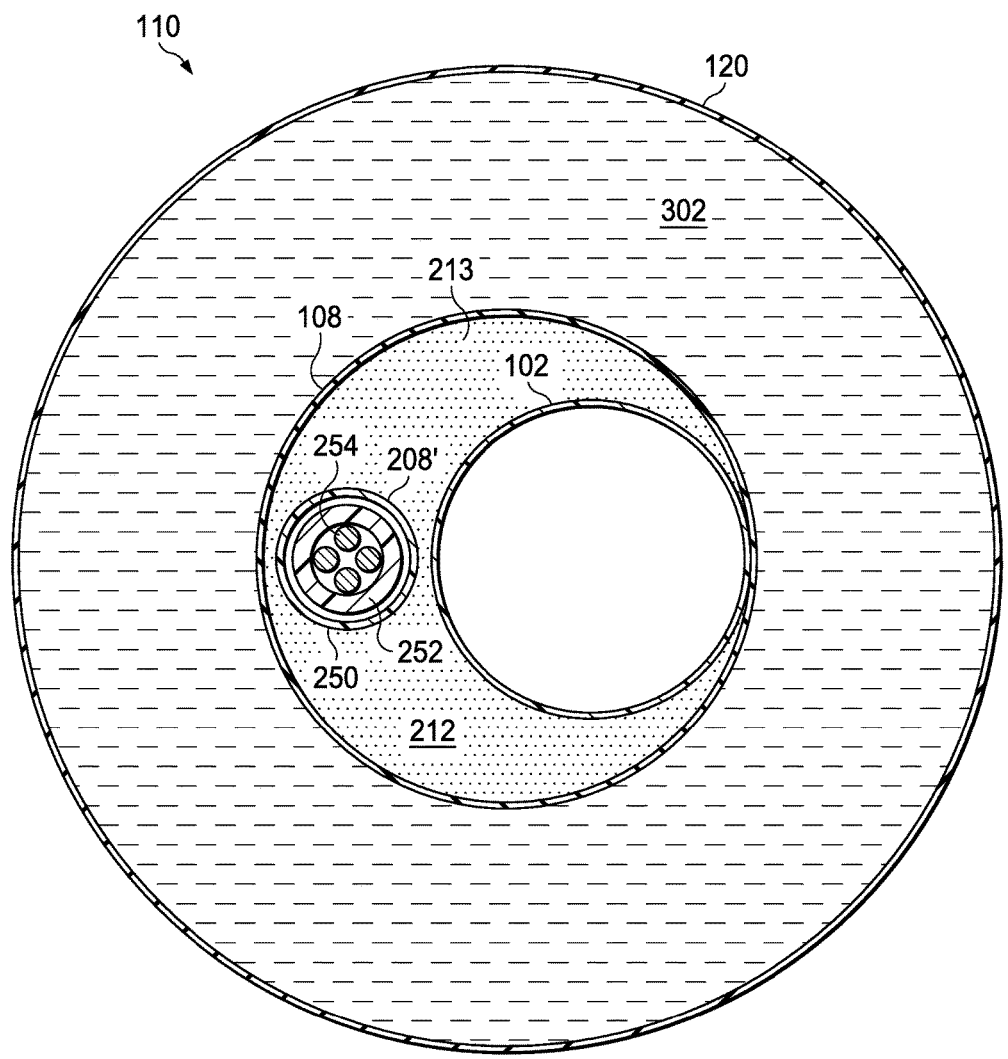

FIG. 3A is a diagram showing an illustrative cross-section of the balloon assembly 110 taken along line 3-3 of FIG. 1A. According to certain illustrative examples, the cross-section includes the balloon outer sleeve 120, the balloon inner sleeve 108, the connection media 208, and the inner member 102. The diameter of the balloon depends on the amount of inflation fluid 302 pumped into the balloon through the proximal junction. For non-distensible balloon materials, the balloon diameter is fixed to a specific diameter. In one embodiment, the non-compliant balloon has a working length of approximately 15 mm and is available in expanded diameters ranging from 2.0 to 4.0 mm in 0.5 mm increments. In one embodiment, the outer diameter of the balloon assembly in the collapsed state is approximately 0.040 inches.

The proximal shaft 104 at the proximal end of the balloon and the mid-shaft 114 at the distal end of the balloon are independent shafts. According to certain illustrative examples, there is not a continuous shaft extending through the interior of the balloon. Rather, the interior of the balloon includes only the connection media 208 and the inner member 102. This provides additional flexibility within the balloon. Moreover, this allows the connection media 208 to float freely within the space 212 between the balloon inner sleeve 108 and the inner member 102. In the illustrated example, the ends of the balloon inner sleeve 108 are sealed to the respective proximal and distal catheter components forming the fluid tight chamber 212 surrounding microcable 208 and inner member 102. In some cases, the space 212 may be filled with air or other gases, while in some cases the space 212 may be filled with a liquid.

As mentioned above, an inflation fluid is used to inflate the balloon when it is appropriately aligned in order to perform various medical tasks such as relieving an arterial occlusion. Thus, the diameter of the balloon outer sleeve 120 changes based on the inflation status of the balloon. As the balloon is non-compliant, the diameter only extends to a certain point. The non-compliant nature of the balloon prevents too much expansion within a patient's artery. The balloon inner sleeve 108 is designed with integrity such that the balloon inner sleeve 108 will not place too great of a pressure on the connection media 208 when the balloon is inflated.

Figure 4A:
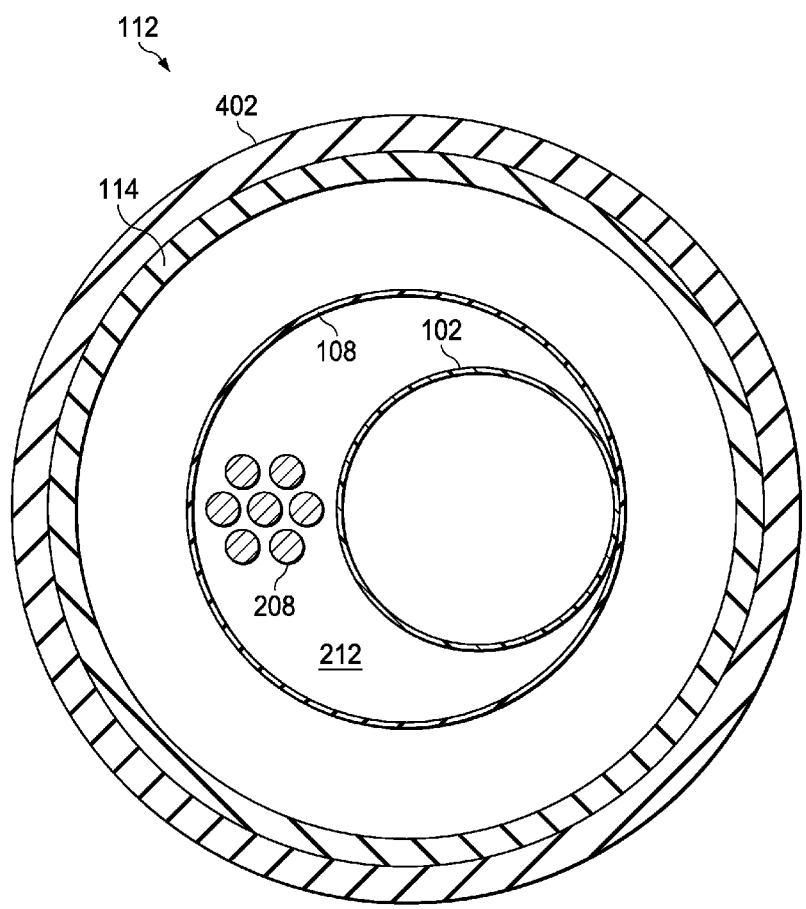
FIGS. 4A and 4B are diagrams showing an illustrative cross-section of a distal junction of a balloon catheter taken along line 4-4 of FIGS. 1A and 1B, respectively, according to one example of principles described herein.
Figure 4B:
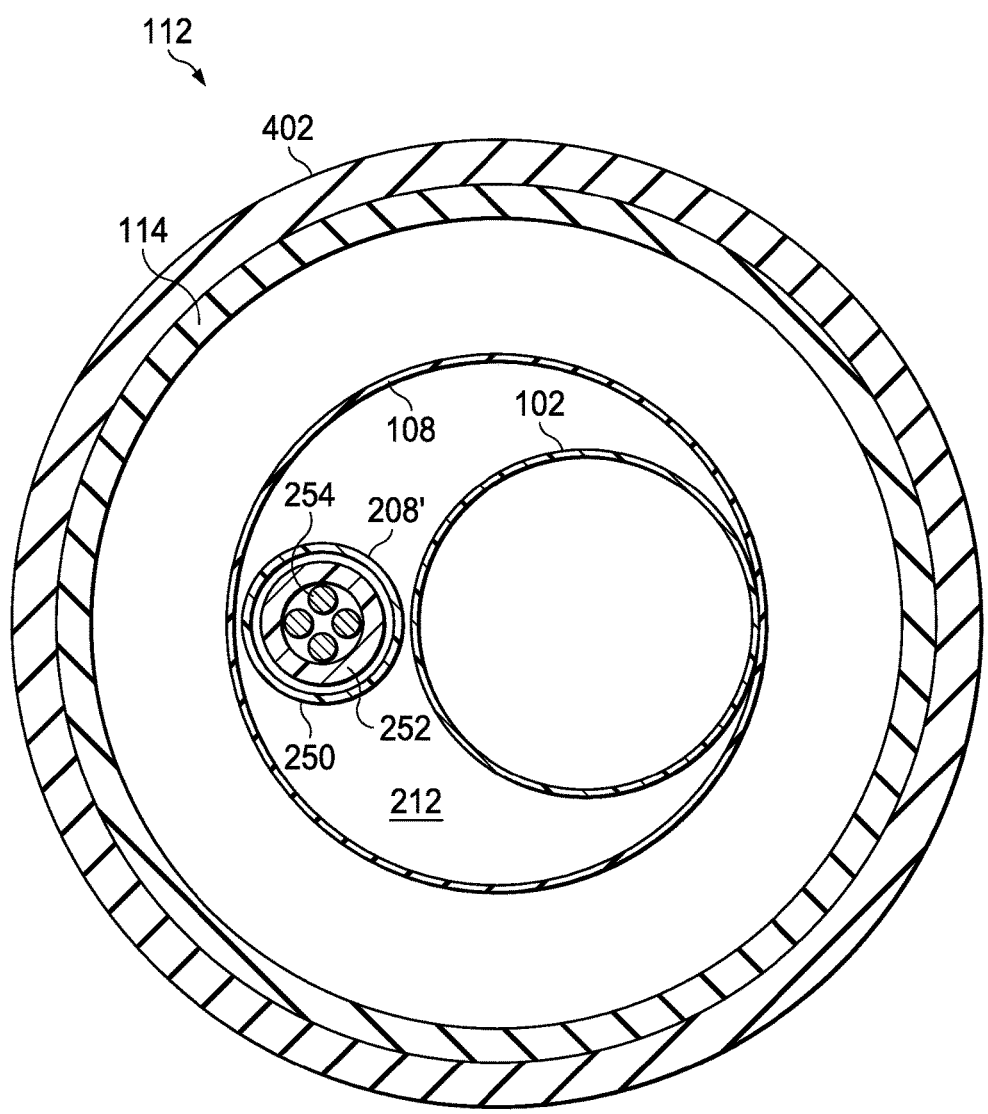

FIG. 4A is a diagram showing an illustrative cross-section of the distal junction 112 of the balloon catheter 100 according to one embodiment of the present disclosure. According to certain illustrative examples, the distal junction 112 connects the balloon to the mid-shaft 114 at the distal end of the balloon. The distal junction 112 includes the inner member 102, the inner balloon sleeve 108, and the space 212 through which the connection media 208 runs. The distal junction 112 further includes a balloon distal leg 402. FIG. 4B illustrates similar features including the rotary drive shaft assembly 208.

The mid-shaft 114 is an independent shaft that is connected adjacent its proximal end to the distal end of the balloon and adjacent its distal end to the sensing device 116. The mid-shaft 114 is also designed to be flexible in order to allow the catheter to effectively traverse a patient's artery. The mid-shaft 114 may have a diameter within the range of 2.5 to 4 French (i.e., 0.83 to 1.33 mm).

The length of the mid-shaft 114 depends on the desired distance between the distal end of the balloon and the sensing device. The length may be long enough so that the sensing device does not interfere with the distal junction as the catheter traverses sharper turns. The length of the mid-shaft may also be short enough so as not to push the sensing device too much deeper into the patient's artery when using the balloon to relieve an arterial occlusion. In one example, the length of the mid-shaft may be a length within a range of 3 to 15 mm with an exemplary range from 5 to 10 mm in length.

The balloon inner sleeve 108 is bonded to the interior of the mid-shaft 114. Additionally, the exterior of the mid-shaft 114 is bonded to the balloon distal leg 402. The balloon distal leg 402 is part of the balloon outer sleeve and is designed to fit securely around the mid-shaft 114. Because the mid-shaft is independent from the proximal shaft, the integrated catheter has an overall greater flexibility. Additionally, the connection media 208 are allowed to float freely through the center of the balloon without comprising the integrity of the balloon. In one aspect, the connection medium 208 comprises a braided microcable having seven individually insulated electrical conductors. In the illustrated embodiment of FIG. 3A, the external braid material has been removed so that each conductor can float independently within the space 212 defined within inner sleeve 108. It will be appreciated that the during the bonding process, the individual conductors will have some slack between the distal and proximal bonding areas such that the conductors can be curved to follow tortuous vessel paths and can migrate over one another under high pressure balloon inflation. The relatively free movement of the conductors within the balloon assembly provides a low profile and highly flexible assembly that inhibits conductor breakage while providing a fluid tight inflation system for high pressure capabilities above 20 ATM.

As mentioned above, the balloon assembly 110 can be used to relieve various types of arterial occlusions. When the balloon assembly 110 is appropriately positioned within a patient's artery, the balloon outer sleeve 120 is then inflated to put pressure on the occlusion. The balloon outer sleeve 120 is typically inflated with an inflation fluid. The inflation fluid is typically a saline fluid as such a fluid is harmless to the patient if it leaks into the artery. The inflation fluid may be pumped into the balloon through an inner lumen of the proximal shaft 104 to a range of 15 to 20 ATM, or even greater depending on material properties of the balloon.

According to certain illustrative examples, the balloon outer sleeve 120 is a non-compliant balloon. A non-compliant balloon is one that is designed to inflate to a particular diameter and not stretch beyond that diameter. This prevents the balloon outer sleeve 120 from expanding too much. This is important because excess expansion could damage a patient's artery. The balloon outer sleeve 120 may also be designed to resist too much axial compression, which could allow the non-compliant balloon outer sleeve 120 to expand farther than desired. Additionally, the balloon outer sleeve 120 may be designed to resist too much axial stretching, which could prevent the balloon outer sleeve 120 from expanding to the desired diameter. In some embodiments, as detailed below in FIGS. 8A-8F, a stent is positioned in a compressed state around the balloon for delivery to a site of stenosis. The balloon may be inflated to plastically expand the stent to open the vessel and the stent can remain in a supporting position after the balloon is deflated.

As mentioned above, the sensing device 116 can be used to image the interior of a patient's artery. Various types of sensing devices may be used. One example of a sensing device 116 is an OCT device. In another form, the sensor can collect information for spectroscopy or photo acoustic imaging. The sensing device 116 may also be a forward looking device that scans forward into the artery rather than outward from the axis towards the arterial walls.

The sensing device 116 may also be an IVUS device. There are two general types of IVUS devices that may be used. The first type of device is a solid state device, also known as a phased array. Solid-state IVUS devices carry a transducer complex that includes an array of ultrasound transducers distributed around the circumference of the device. The transducers are connected to a set of transducer controllers. The transducer controllers select individual transducers for transmitting an ultrasound pulse and for receiving the echo signal. By stepping through a sequence of transmit-receive pairs, the solid-state IVUS system can synthesize the effect of a mechanically scanned transducer element, but without moving parts. Because there is no rotating mechanical element, the transducer array can be placed in direct contact with the blood and vessel tissue with minimal risk of vessel trauma. Furthermore, the interface is simplified because there is no rotating element. The solid-state scanner can be wired directly to the imaging system with a simple electrical cable and a standard detachable electrical connector.

In the example of a transducer array as a sensing device, the connection medium running through the catheter shafts includes the electrical cables that communicate data between the transducer array and external processing systems. The number of wires and cables comprising the connection media may depend on the type of transducer array. For example, a 64 bit array may use more cables than a 32 bit array. Additionally, various multiplexing functions may be used to reduce the number of wires running through the catheter shafts.

The second general type of IVUS device is a rotational device. A typical rotational IVUS device includes a single ultrasound transducer element located at the tip of a flexible driveshaft. The transducer can be a traditional planar PZT type transducer or the transducer can a be focused transducer such as a PMUT type device that permits Focused Acoustic Computed Tomography (FACT). In one aspect, the transducer is positioned distally of the balloon while in another embodiment the transducer is positioned within the inner sleeve 108 within the balloon assembly. The driveshaft spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In the example of a rotational array as the sensing device 116, the connection media running through the catheter shafts includes a driveshaft lumen that comprises the plastic sheath 250 surrounding a driveshaft 252 used to drive the rotational array. Additionally, the connection media include any electrical cables 254 that communicate data between the transducer array and external processing systems.

FIGS. 5A-5C are diagrams showing an illustrative insertion of a balloon catheter into a patient. The present invention can be used in a variety of lumens, vessels or passages in the body including, but not limited to, arteries such as coronary, carotid or peripheral, veins, structural heart, digestive system, organs and brain. According to certain illustrative examples, a guide-wire 506 is fed into a patient's artery 504. In one aspect, a guidewire having a diameter of approximately 0.014 inches can be utilized. The catheter can then be moved along that guide-wire 506 deeper into the patient's artery 504.

FIG. 5A is a diagram 500 showing an integrated catheter being pushed into a patient's artery 504. The tip of the catheter 502 can be designed to facilitate such entry. Although not shown, it will be understood that in some applications a guiding catheter having a minimum internal diameter of approximately 6 French (i.e., 0.066 inches or 2 mm) may be used to facilitate placement of the sensing balloon catheter. At this point, the balloon is not inflated. The catheter is pushed into the artery 504 until the distal junction of the balloon enters the artery 504. The catheter 502 is then pushed further into until the proximal junction enters the artery 504. Thereafter, the catheter 502 is pushed further into the artery with the proximal shaft 512 extending outside the artery 504 and outside the patient.

FIG. 5B is a diagram 510 showing the catheter 502 moving through the patient's artery. According to certain illustrative examples, the catheter 502 traverses the artery 504 as a doctor views the data obtained by the sensing device. This data will inform the doctor if there is some type of arterial occlusion 508. Upon finding such an occlusion 508, the catheter 502 is pushed further into the patient a known distance such that the balloon is aligned with the occlusion 508.

FIG. 5C is a diagram 520 showing the integrated balloon catheter 502 inflated in order to relieve an arterial occlusion. According to certain illustrative examples, upon being appropriately aligned, the balloon is inflated in order to relieve the occlusion. As mentioned above, this is done by pumping an inflation fluid through an inner lumen of the proximal shaft 512. As the proximal shaft 512 is flexible, it bends appropriately in order to enter and traverse the artery 504 without causing damage.

Figure 6:
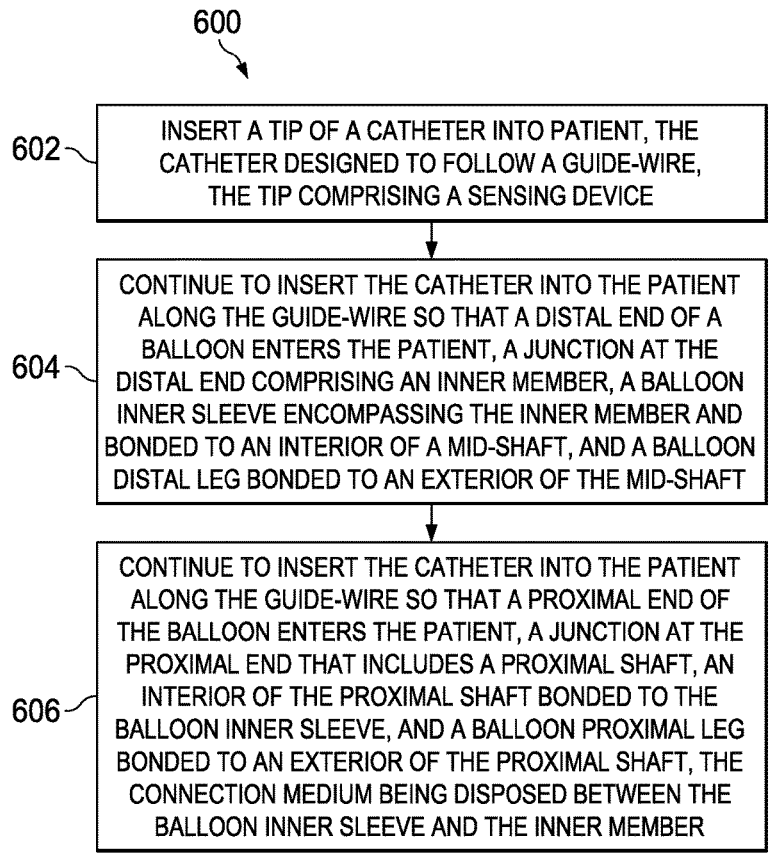
FIG. 6 is a flowchart describing an illustrative method for utilizing a therapeutic sensing catheter within a patient, according to one example of principles described herein.

FIG. 6 is a flowchart showing an illustrative method 600 for inserting a balloon catheter into a patient. According to certain illustrative examples, the method includes inserting 602 a tip of a catheter into a patient, the catheter designed to follow a guide-wire, the tip comprising a sensing device. The method further includes continuing 604 to insert the catheter into the patient along the guide-wire so that a distal end of a balloon enters the patient, a junction at the distal end comprising an inner member, a balloon inner sleeve encompassing the inner member and bonded to an interior of a mid-shaft, and a balloon distal leg bonded to an exterior of the mid-shaft. The method further includes continuing 606 to insert the catheter into the patient along the guide-wire so that a proximal end of the balloon enters the patient, a junction at the proximal end that includes a proximal shaft, an interior of the proximal shaft bonded to the balloon inner sleeve, and a balloon proximal leg bonded to an exterior of the proximal shaft, the connection medium being disposed between the balloon inner sleeve and the inner member.

Figure 7:
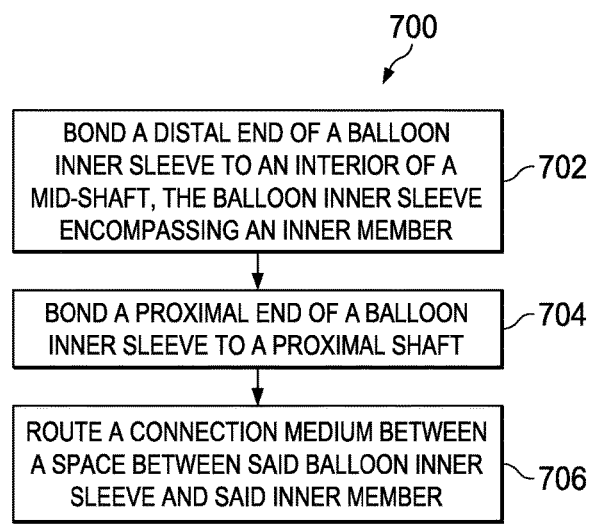
FIG. 7 is a flowchart showing an illustrative method for fabricating a sensing balloon catheter, according to one example of principles described herein.

FIG. 7 is a flowchart showing an illustrative method for fabricating a balloon catheter. According to certain illustrative examples, the method includes bonding 702 a distal end of a balloon inner sleeve to an interior of a mid-shaft, the balloon inner sleeve encompassing an inner member. The method further includes bonding 704 a proximal end of the balloon inner sleeve to a proximal shaft, and routing 706 a connection medium between a space between said balloon inner sleeve and said inner member.

FIGS. 8A-8E illustrate the insertion of an integrated therapeutic and imaging catheter or integrated catheter 800 into a patient. The integrated catheter 800 includes a balloon assembly 802 and an imaging device 803, which are substantially similar to the balloon assembly 110 and the sensing device 116, respectively, except for any differences noted herein. The inner sleeve 804 of the integrated catheter 800 is substantially similar to the inner sleeve 108 except for any differences noted herein. As mentioned above in relation to the inner sleeve 108, in some embodiments, the inner sleeve 804 has high pressure capability greater than 20 ATM, which makes the balloon assembly 802 suitable for non-compliant post dilatation. For example, FIGS. 8A-8E illustrate the use of the integrated catheter 800 to access an intravascular lesion 806, assess the intravascular lesion, and treat the intravascular lesion using a treatment device, such as an expandable stent 808, according to one embodiment of the present disclosure.

In the pictured embodiment, the treatment device comprises the expandable stent 808. In other embodiments, the treatment device may comprise any of a variety of expandable devices shaped and configured to be carried on the balloon assembly 802 for the treatment of intratubular lesions, e.g., intravascular lesions. For example, the treatment device may comprise a scaffolding device, a valve device, a filtering device, a stent graft, a sensor device, an ablation device, a drug delivery or elution device. In some instances, the treatment device may comprise a resorbable device, such as, by way of non-limiting example, a resorbable stent. In some instances, the treatment device may be designed to indefinitely remain in the vessel after removable of the catheter 800. In other instances, the treatment device may be designed for removal along with the catheter 800 or removal at a later time.

FIG. 8A illustrates the integrated catheter 800 being advanced into a patient's artery 810. Initially, a guide-wire 812 is fed into the artery 810. In one aspect, a guidewire having a diameter of approximately 0.014 inches can be utilized. The catheter can then be moved along the guide-wire 802 deeper into the patient's artery 504. During insertion of the catheter 800 into the vessel 810, the balloon assembly 802 is not inflated and maintains a low profile in an unexpanded condition. A distal end 814 of the catheter 800 can be designed to facilitate entry and progress through the artery 810. For example, the distal end 814 may be tapered.

As shown in FIG. 8A, the catheter 800 is pushed into the artery 810 until the imaging device 803 and a distal junction 816 of the balloon assembly 802 enters the artery 810. The catheter 800 is then pushed further into the artery 810 until a proximal junction 818 of the balloon assembly 802 enters the artery 810. Thereafter, the catheter 800 is pushed further into the artery 810 with a proximal shaft 820 extending outside the artery 810 and outside the patient.

FIG. 8B illustrates the catheter 800 moving through the lesion 806 in the patient's artery 810. The imaging device 803 can be used to detect and assess the lesion 806. The lesion 806 includes a proximal end 825 and a distal end 830, as well as a length L1 extending from the proximal end 825 to the distal end 830. As the catheter 502 traverses the artery 810, a healthcare professional can view the data obtained by the imaging device 803 to assess the health of the vessel. The imaging data can inform the doctor if there is some type of intravascular lesion or injury, such as, by way of non-limiting example, the intravascular lesion 806. The imaging data may also relay other vascular characteristics, such as, by way of non-limiting example, the path and/or tortuosity of the artery 810, the regularity or irregularity of the vessel walls within the artery 810, and various characteristics about the blood flow within the artery 810. Upon visualizing the lesion 806, the catheter 800 is advanced further into the artery 810 until the balloon assembly 802 is aligned with the occlusion 806. The imaging device 803 can continue to image the vessel as the distal end 814 of the catheter 800 travels through the lesion 806, thereby providing the healthcare professional with an accurate assessment of the location of the balloon assembly 802. In particular, the imaging device 803 is positioned a known distance D1 from the balloon assembly 802, which allows a healthcare professional to advance and/or retract the catheter 800 the known distance to position the balloon assembly 802 relative to whatever intravascular position the imaging device 803 is imaging at a given time.

The imaging device 803 can also be used to facilitate placement of the balloon assembly 802 relative to the lesion 806. In the illustrated example, the lesion 806 is an intravascular occlusion that requires reduction and stenting as treatment. As shown in FIGS. 8B and 8C, as the imaging device 803 travels through the lesion, the image data relayed by the imaging device 803 can inform the healthcare professional of various anatomic characteristics within the artery 810, such as, by way of non-limiting example, the length L1 of the lesion 806, the luminal contours of the lesion 806 (e.g., the intraluminal diameter of the artery 810 proximal, adjacent, and distal to the lesion 806), and characteristics of the blood flow through the lesion 806. Using this imaging data, the healthcare professional can advance the catheter 800 an appropriate distance forward to accurately position the unexpanded balloon assembly 802 and overlying stent 808 within the lesion 806. The stent 808 includes a length L2 extending from a proximal stent end 835 to a distal stent end 840. The healthcare professional can assess whether the length L2 of the stent is appropriate to treat the lesion 806, which has the length L1. In addition, the healthcare professional may verify that the diameter of the stent is appropriate to treat the lesion 806. If the stent 808 is comparatively too short, too long, too wide, or too slender to appropriately treat the lesion 806, the catheter 800 may be removed and replaced with a catheter carrying a correctly-sized stent, thereby avoiding the potential stent failure or collapse that may accompany implantation of an inappropriately-sized stent.

FIG. 8C illustrates the expansion of the balloon assembly 802 and the stent 808 within the lesion 806 in the patient's artery 810. After the healthcare professional advances the balloon assembly 820 and the stent 808 (in an unexpanded condition) appropriately within the lesion 806, the healthcare professional may inflate the balloon assembly 802 to both relive the occlusion caused by the lesion 806 and expand the stent 808 to maintain the new patency of the artery 810 at the location of the lesion 806. As mentioned above, this may be done by pumping an inflation fluid through an inner lumen of the proximal shaft 820 of the catheter 800. As the balloon assembly 802 is inflated under a high pressure, typically in the range of 15-25 ATM, the stent 808 assumes an expanded condition and flattens the lesion 806 against inner walls of the artery 810.

Figure 8D:
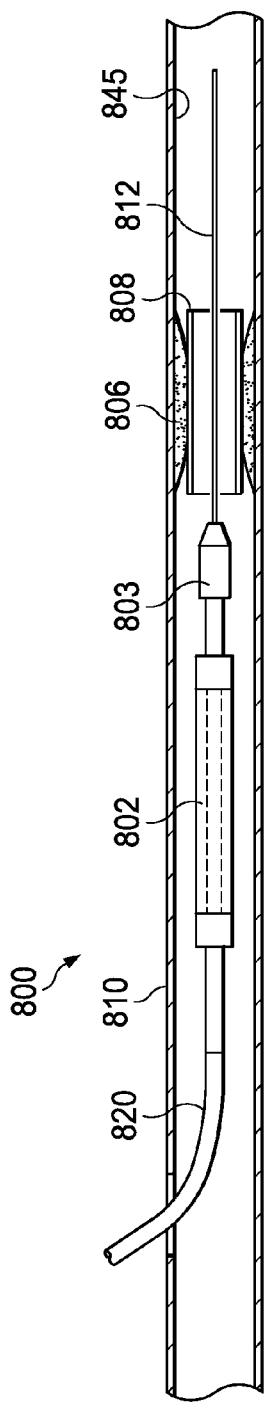

FIG. 8D illustrates the withdrawal of the balloon assembly 802 from the lesion 806 after initial deployment of the stent 808 within the lesion 806. The healthcare professional may deflate the balloon assembly 802 and retract the catheter 800 until the imaging device 803 is positioned proximal to the stent 808. The healthcare professional can use imaging data received by the imaging device 803, now positioned proximal to the lesion 806 and the stent 808, to assess the expansion and deployment of the stent 808. In particular, the imaging data allows the healthcare professional to verify appropriate stent apposition against the lesion 806 and expansion within the artery 810. Occasionally, as shown in FIG. 8D, the expansion of the stent 808 is insufficient to adequately treat the lesion 806. For example, in the pictured embodiment, the stent 808 has not fully expanded to compress the lesion 806 against luminal walls 845 of the artery 810. Instead, the lesion 806 remains partially intact and capable of at least partially occluding flow through the artery 810. The imaging device 803 can convey this information via imaging data to the healthcare professional.

Figure 8E:
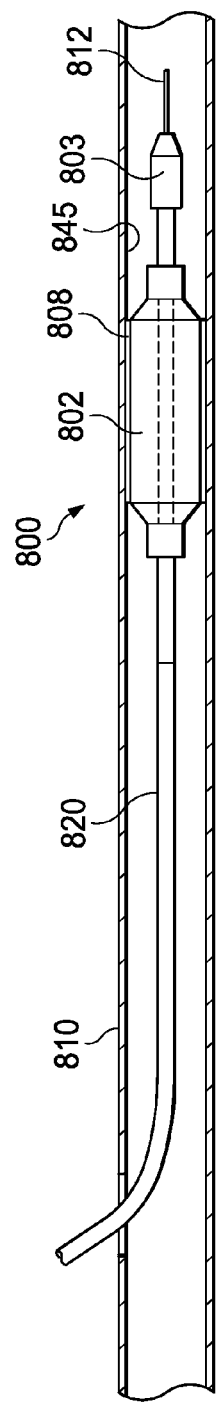

FIG. 8E illustrates the reinsertion and re-expansion of the balloon assembly 802 within the lesion 806. After assessing the stent deployment, if the healthcare professional desires to increase the expansion of the stent 808 and further decrease the profile of the lesion 806, the healthcare professional may re-advance the catheter 800 and re-position the balloon assembly within the stent 808 and the lesion 806. As shown in FIG. 8E, the balloon assembly 802 may be re-inflated at a higher pressure to further expand the stent 808, thereby improving the stent apposition and/or expansion against the luminal walls 845 of the artery 810.

For example, if the initial inflation pressure was 17 ATM, the subsequent inflation pressure may be 20 ATM. In another example, if the initial inflation pressure was 20 ATM, the subsequent inflation pressure may be 25 ATM. Other changes in pressure between the initial and subsequent pressure are contemplated. In some embodiments, the subsequent pressure may be greater than the initial pressure by a predetermined percentage. For example, in one instance, the subsequent inflation pressure may be at least 25% greater than the initial inflation pressure. Other predetermined percentage increases are contemplated. In some embodiments, the healthcare provider may select the change or delta between the initial pressure and the subsequent pressure depending upon the desired degree of further expansion of the treatment device.

Figure 8F:
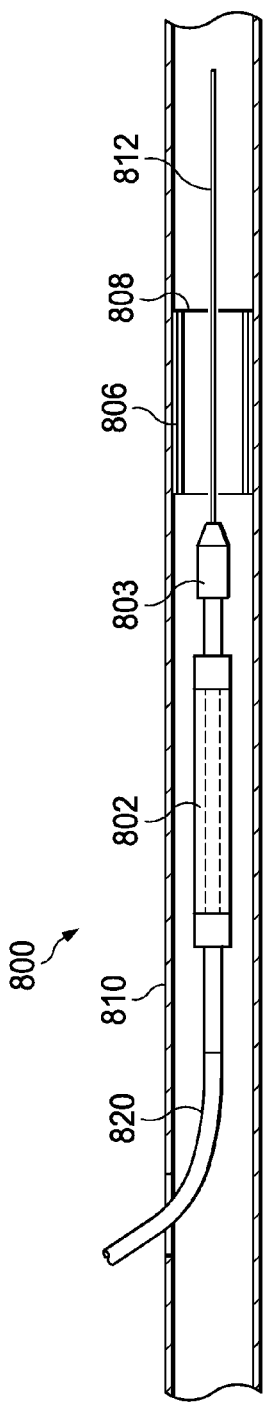

FIG. 8F illustrates the withdrawal of the balloon assembly 802 from the lesion 806 after the secondary expansion of the stent 808 within the lesion 806. The healthcare professional may once again deflate the balloon assembly 802 and retract the catheter 800 until the imaging device 803 is positioned proximal to the stent 808. The healthcare professional can use imaging data received by the imaging device 803 to assess the expansion and deployment of the stent 808. In particular, the imaging data allows the healthcare professional to verify appropriate stent apposition against the lesion 806 and expansion within the artery 810. If the imaging data indicates appropriate deployment of the stent 808 (i.e., appropriate positioning, expansion, and apposition), then the healthcare professional may withdraw the catheter 800 from the artery 810 (and the patient's body).

In another embodiment, the catheter may comprise a balloon assembly, an imaging device, and an ablation device. In other embodiments, the catheter may comprise a balloon assembly, an imaging device, and an electrical stimulation device. In some embodiments, these treatment devices could be used to denervate target tissue. As described above with reference to FIGS. 8A-8F, the healthcare professional may inflate the balloon assembly at increasingly higher pressures in combination with imaging to verify the accurate positioning, repositioning, and real-time use of these treatment devices.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

I claim:

1. An integrated therapeutic and imaging catheter, comprising:
    an inner member defining a guidewire lumen;
    a balloon assembly comprising:
        an inner sleeve defining a further lumen, wherein the inner member and a connection medium are positioned within the further lumen such that the inner sleeve completely circumferentially surrounds the inner member and the connection medium, wherein the connection medium is disposed between the balloon inner sleeve and the inner member, wherein the inner sleeve is configured to protect the connection medium when the balloon assembly is inflated; and
        an outer sleeve surrounding the inner sleeve;
        a treatment device mounted about the balloon assembly; and
    an imaging device disposed distal to the balloon assembly and coupled to the connection medium.

2. The catheter of claim 1, wherein the connection medium is positioned to move freely within a space between the inner member and the inner sleeve.

3. The catheter of claim 1, further comprising a proximal junction comprising:
    a proximal shaft, an interior of the proximal shaft bonded to the inner sleeve; and
    a balloon proximal leg bonded to an exterior of the proximal shaft.

4. The catheter of claim 3, wherein the proximal shaft comprises an axial dual lumen shaft.

5. The catheter of claim 4, wherein the inner sleeve is disposed between an outer lumen of the dual lumen shaft and an inner lumen of the dual lumen shaft.

6. The catheter of claim 3, further comprising a mid-shaft independent from the proximal shaft, wherein the inner sleeve is bonded to an interior of the mid-shaft and the mid-shaft connects the balloon assembly and the imaging device.

7. The catheter of claim 1, wherein the balloon assembly is non-compliant.

8. The catheter of claim 1, wherein the inner sleeve is structurally arranged to protect the connection medium when the balloon assembly is inflated at pressures above 20 ATM.

9. The catheter of claim 1, wherein the connection medium comprises one of an electrical conduction wire and an optical fiber.

10. The catheter of claim 9, wherein the connection medium carries data produced by the imaging device.

11. The catheter of claim 9, wherein the connection medium is structurally arranged to power the imaging device.

12. The catheter of claim 1, wherein the connection medium comprises a driveshaft configured to drive the imaging device at a distal end of the balloon assembly.

13. The catheter of claim 1, wherein the treatment device is an expandable stent surrounding the balloon assembly and configured to expand when the balloon assembly is inflated.

14. The catheter of claim 1, wherein the inner sleeve is structurally arranged to elastically deform inwardly under high operating pressures.

15. The catheter of claim 14, wherein the inner sleeve is structurally arranged to elastically reform to its original shape when the high operating pressures are discontinued.

16. The catheter of claim 1, further comprising a guidewire extending through the guidewire lumen.

17. The catheter of claim 1, wherein the imaging device comprises an intravascular ultrasound transducer.

18. The catheter of claim 1, wherein the imaging device comprises an optical coherence tomography device.

19. The catheter of claim 1, wherein the inner sleeve comprises a multi-layer structure.

\* \* \* \* \*